United States Patent [19]

Dubroff

[11] Patent Number: 4,642,113
[45] Date of Patent: * Feb. 10, 1987

[54] INTRAOCULAR LENSES

[76] Inventor: Seymour Dubroff, 4000 Massachusetts Ave., Apt. 1422, Washington, D.C. 20016

[*] Notice: The portion of the term of this patent subsequent to Mar. 18, 2003 has been disclaimed.

[21] Appl. No.: 752,012

[22] Filed: Jul. 8, 1985

Related U.S. Application Data

[63] Continuation of Ser. No. 496,529, May 23, 1983, abandoned, which is a continuation of Ser. No. 230,279, Jan. 30, 1981, abandoned.

[51] Int. Cl.$^4$ ................................................. A61F 2/16
[52] U.S. Cl. .......................................................... 623/6
[58] Field of Search ................................... 623/6; 3/13

[56] References Cited

U.S. PATENT DOCUMENTS

| | | | |
|---|---|---|---|
| 4,159,546 | 7/1979 | Shearing | 623/6 |
| 4,174,543 | 11/1979 | Kelman | 623/6 |
| 4,242,760 | 1/1981 | Rainin | 623/6 |
| 4,244,060 | 1/1981 | Hoffer | 623/6 |
| 4,366,582 | 1/1983 | Faulkner | 623/6 |

OTHER PUBLICATIONS

"Experience with Twelve Cases of Intra-Ocular Anterior Chamber Implants for Aphakia" by J. Boberg-Ans, British Journal of Ophthalmology, vol. 45, No. 1, Jan. 1961, pp. 37–43.
AM Intra-Ocular Implant Soc. J.-vol. V, Oct. 1979, p. 557 (Fig. 1 Simcoe Two-Loop & —3—Loop Styles relied upon).
The Simcoe Posterior Chamber Lens (5 page Advertisement Brochure by Cilco), Cilco, Inc., 1616 13th Ave., Huntington, West Virginia, 25701, Feb. 1980.
The Intraocular Implant Lens Development and Results with Special Reference to the Binkhorst Lens (Book) by M. E. Nordlohne, 2nd Edition, The Williams & Wilkins Co., Baltimore, 1975, pp. 14–20 (S-shaped Barraquer Lens in Fig. 4 relied upon).

Primary Examiner—Ronald L. Frinks
Attorney, Agent, or Firm—Epstein & Edell

[57] ABSTRACT

An intraocular lens for implant in the eye, particularly in the anterior chamber, includes a lens body and a plurality of positioning members having proximal portions extending from the lens body supporting flexible, resilient curved filaments with the proximal portions having a width greater than the filaments to provide stable positioning in the eye and prevent pupillary capture of the lens body. In another embodiment, an intraocular lens has at least three flexible, resilient, fixation filaments extending from the periphery of a lens body and having continuous curving configurations, the fixation filaments being positioned to prevent pupillary capture of the lens body.

3 Claims, 12 Drawing Figures

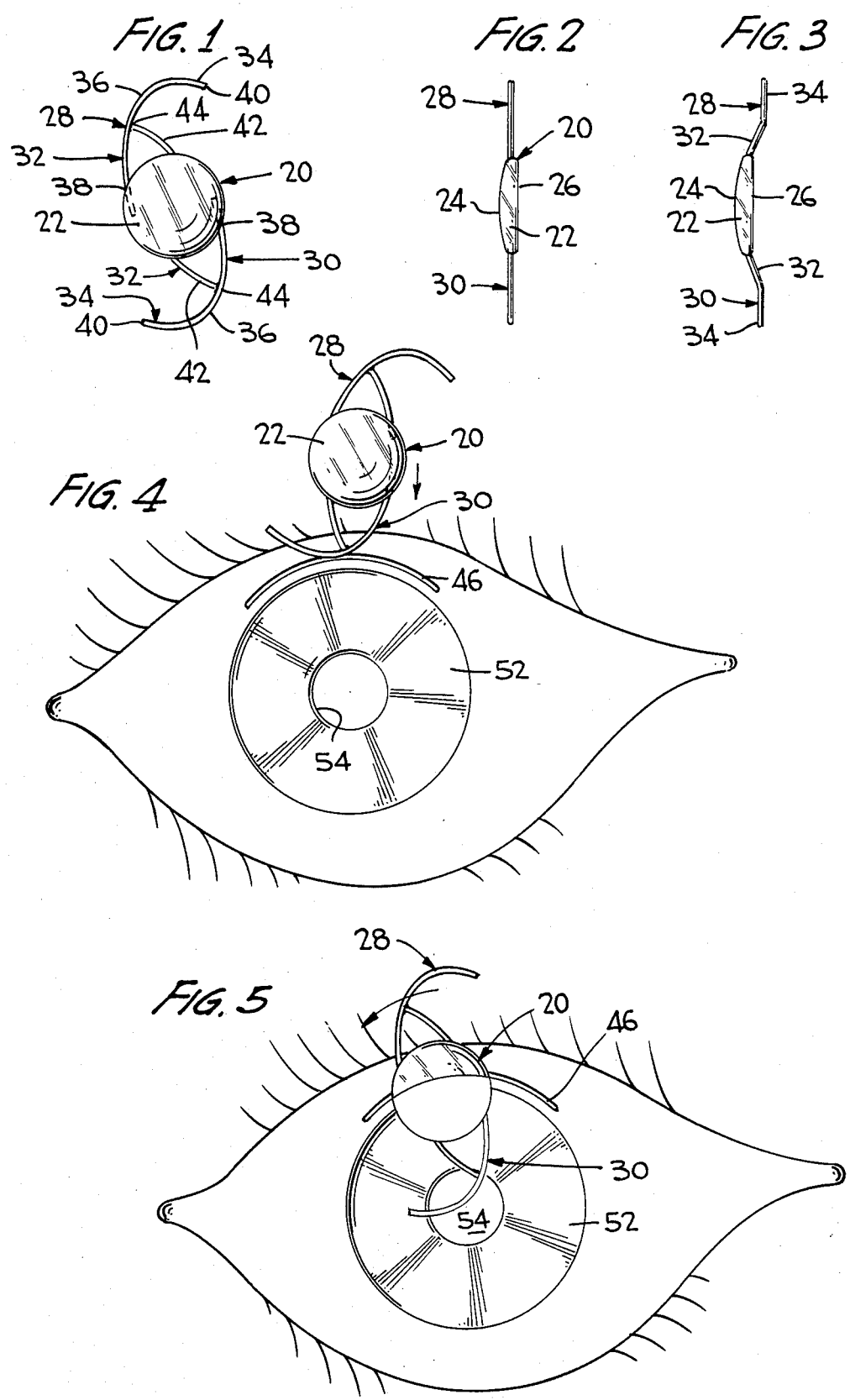

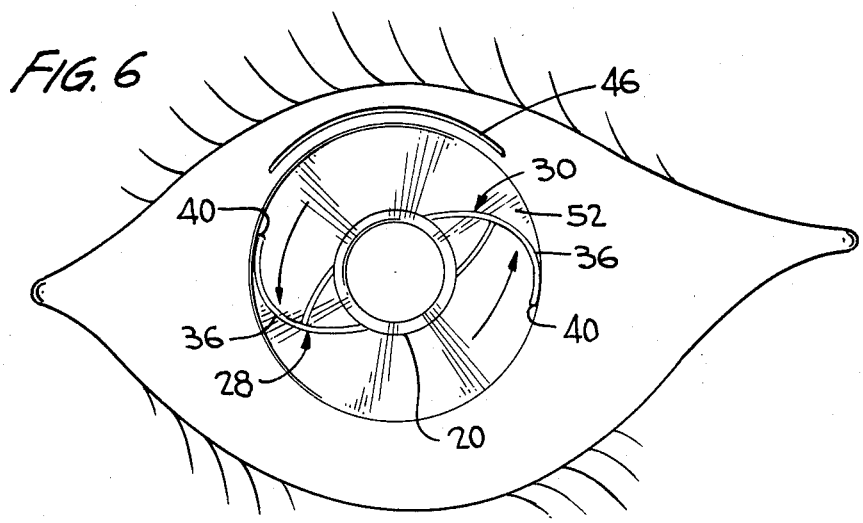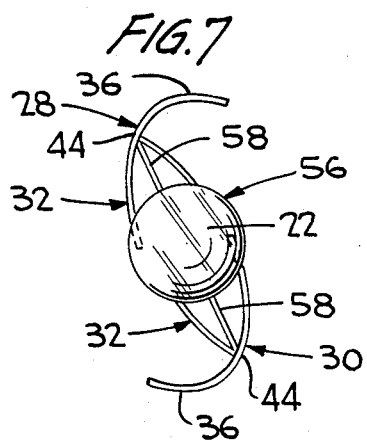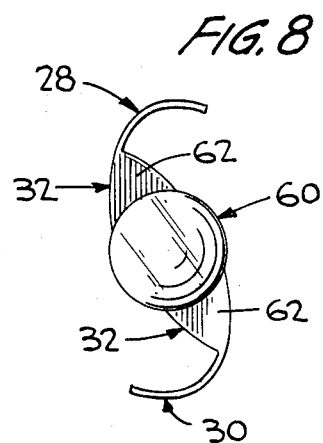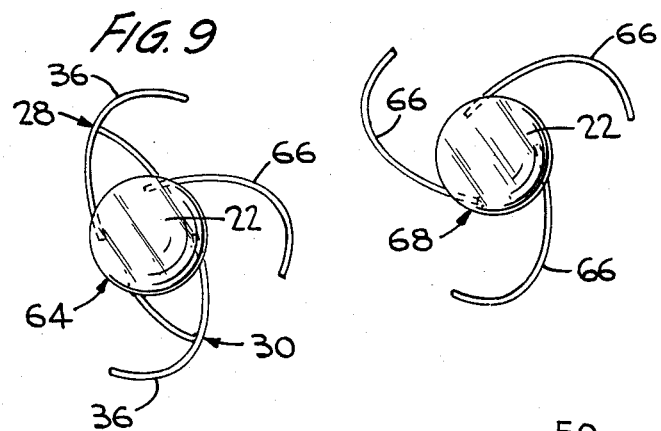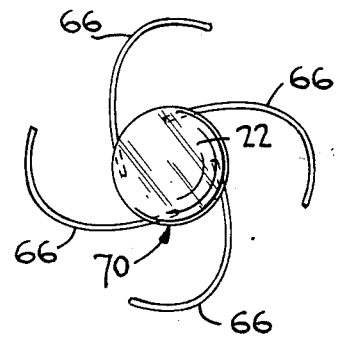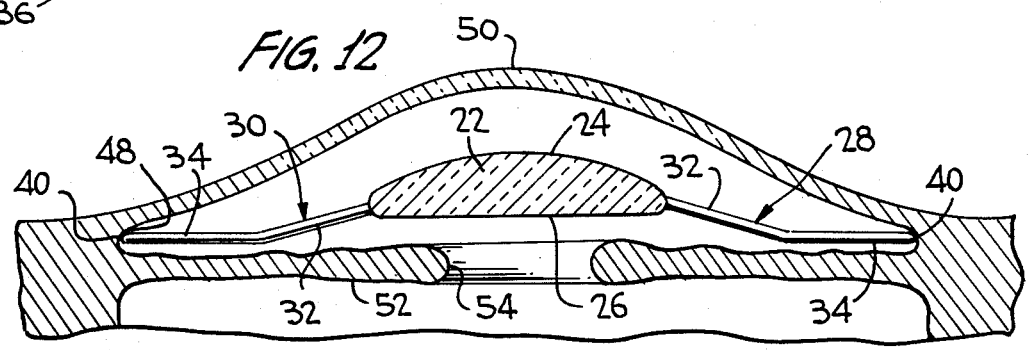

INTRAOCULAR LENSES

This application is a continuation, of application Ser. No. 496,529, filed May 23, 1983. which is a continuation of Application Ser. No. 230,279 filed Jan. 30, 1981 both now abandoned.

BACKGROUND OF THE INVENTION

1. Field of the Invention

The present invention pertains to artificial lenses for the eye and, more particularly, to intraocular lenses for surgical implantation in the eye.

2. Discussion of the Prior Art

The implantation of an artificial intraocular lens in an eye after removal of the natural lens due to a blindness-causing condition, such as cataract, has become an accepted practice. Such intraocular lenses are normally positioned in the posterior chamber of the eye, secured to the iris, or positioned in the anterior chamber of the eye. Anterior chamber intraocular lenses are desirable due to their advantages of requiring reduced manipulation for proper placement and of being suitable for use with intracapsular and extracapsular natural lens removal; however, in the past, anterior chamber intraocular lenses have suffered the disadvantages of requiring a precise measurement of the diameter of the anterior chamber of cornea to select the appropriate size implant and of the implanted intraocular lens irritating the cornea by riding thereagainst due to the insufficient flexibility of existing anterior chamber intraocular lenses. If the intraocular lens implanted is too small, movement of the intraocular lens in the anterior chamber can cause corneal irritation; and, if the intraocular lens implanted is too large, the UGH syndrome, hyphema, eye tenderness can occur. Accordingly, prior art anterior chamber intraocular lenses have had to be available in all sizes to the surgeon, and the surgeon must accurately determine the diameter of the anterior chamber before insertion of the intraocular lens or subject the patient to the trauma of implanting and removing intraocular lenses on a trial and error basis to find the proper size intraocular lens.

Accordingly, recently, it has become common to utilize posterior chamber intraocular lenses; however, the use of such lenses inherently requires precise and difficult manipulation of the intraocular lens for placement behind the iris and, additionally, problems arise when the lens capsule is punctured or removed during removal of the natural lens. Thus, implantation of posterior chamber lenses effectively has been limited due to the surgical skill required in removal of the natural lens without puncturing the lens capsule and the surgical skill required to properly manipulate the implant lens for proper positioning in the posterior chamber. Even then, decentered lenses are not rare.

The practice of implanting intraocular lenses after natural lens removal due to cataract or other blindness-causing conditions is ever increasing; and, as more surgeons utilize this practice, rather than utilizing spectacles or contact lenses to provide focusing power after removal of the natural lens, the need for an intraocular lens that can be simply implanted with a minimum of trauma and minimum discomfort to the patient during surgery and thereafter has increased greatly. Thus, there has recently been a return to the use of anterior chamber intraocular lenses and much effort has been expended to design anterior chamber intraocular lenses of a nature to be easily implanted in the anterior chamber via a single insertion. However, such prior art anterior chamber intraocular lenses have had the disadvantages of often not being sufficiently flexible to be comfortably worn by a patient without irritation, not permitting simple implantation, or have created problems with pupillary capture.

SUMMARY OF THE INVENTION

Accordingly, it is a primary object of the present invention to overcome the above mentioned disadvantages of the prior art by providing an intraocular lens for positioning in the anterior chamber of the eye of an extremely soft, flexible nature minimizing the opportunity for pupillary capture.

Another object of the present invention is to utilize flexible, resilient curved filaments extending from a lens body of an intraocular lens to facilitate implanting of the anterior chamber.

A further object of the present invention is to prevent pupillary capture and reduce twisting or turning of an intraocular lens in the anterior chamber of the eye by utilizing positioning members having distal portions formed of flexible, resilient filaments and proximal portions having a width greater than the filaments, the proximal portions preferably having a tapered or wedge-like configuration.

The present invention has an additional object in that twisting or turning of an intraocular lens in the anterior chamber of the eye is minimized by utilizing at least three flexible, resilient fixation filaments extending from a lens body and having a continuously curving configuration.

Some of the advantages of the present invention over the prior art are that a single size intraocular lens according to the present invention can be utilized for insertion in the anterior chamber of most normal eyes, the intraocular lens is easily implanted, the intraocular lens reduces corneal irritation and is comfortable in place with decreased post operative tenderness, and the intraocular lens has reduced weight and does not have large, bulky, solid foot plates as do prior art anterior chamber intraocular lenses.

The present invention is generally characterized in an intraocular lens for implant in an eye including a lens body, and a plurality of positioning members disposed on the lens body, each of the positioning members having a distal portion formed of a flexible, resilient filament having a curved configuration and a proximal portion supporting the distal portion and extending from the lens body and having a width greater than the filament whereby the distal portions provide stable positioning of the intraocular lens in the eye and the proximal portions prevent pupillary capture of the intraocular lens.

The present invention is further generally characterized in an intraocular lens for implant in the anterior chamber of an eye including a lens body, and a plurality of flexible, resilient, fixation filaments extending from the periphery of the lens body to terminate at free ends, the fixation filaments having a continuous curving configuration with a maximum radius of curvature adjacent the periphery of the lens body and a minimum radius of curvature adjacent the free ends.

Other objects and advantages of the present invention will become apparent from the following description of the preferred embodiments taken in conjunction with the accompanying drawings.

BRIEF DESCRIPTION OF THE DRAWINGS

FIG. 1 is a plan view of an intraocular lens according to the present invention.

FIG. 2 is a side elevation of the intraocular lens of FIG. 1.

FIG. 3 is a side elevation of the intraocular lens of FIG. 1 with a vaulted configuration.

FIGS. 4, 5 and 6 illustrate the insertion of the intraocular lens of the present invention in the anterior chamber.

FIGS. 7, 8, 9, 10 and 11 are plan views of various modifications of the intraocular lens of the present invention.

FIG. 12 is a cross sectional view of an intraocular lens according to the present invention in the anterior chamber of the eye.

DESCRIPTION OF THE PREFERRED EMBODIMENTS

An intraocular lens 20 according to the present invention is shown in FIG. 1 and includes a lens body 22 having a generally circular periphery and made of any suitable material for focusing light, preferably a nondegradable and nontoxic plastic. For example, the lens body can be made of polymethylmethacrylate and constructed to a desired prescription and configuration. The lens body 22 has an anterior surface 24, normally having a convex shape, and a posterior surface 26, normally having a flat or planar shape, such that the lens body serves to focus light on the retina in the manner of the natural lens of the eye.

Positioning members 28 and 30 are disposed at diametrically opposed positions on the lens body, and each positioning member includes a proximal portion 32 extending from the periphery of the lens body and a distal portion 34 supported by the proximal portion and including a flexible, resilient fixation filament 36. In the embodiment of FIG. 1, the fixation filament 36 has a fixed end 38 secured to the lens body at the periphery thereof and terminates at a free end 40, and the fixation filament forms part of the proximal portion 32 of the positioning members as well as the distal portion 34. The fixation filaments 36 can have any desirable shape in cross section but are preferably round to provide smooth surfaces, and the filaments have a continuous curving configuration with a maximum radius of curvature at a fixed ends 38 adjacent the periphery of the lens body and a minimum radius of curvature at the free ends 40. The proximal portion 32 of each positioning member is defined on one side by fixation filament 36 and on the other side by a strut filament 42 extending from the periphery of the lens body to intersect the fixation filament at a point 44 spaced from the free end 40 such that the proximal portion, defined as the part of positioning members between the intersection point 44 and the periphery of the lens body, has a width greater than the fixation filament. The proximal portions 32 have a point of maximum width adjacent the lens body 22 and smoothly taper to a point of minimum width at the intersection point 44 to have a wedge-like configuration to prevent pupillary capture of the intraocular lens 20 upon placement in the eye.

The fixation and strut filaments are formed of a very flexible, resilient material such that the resilience or memory characteristic of the material permits the filaments to be compressed upon placement in the anterior chamber of the eye with the free ends 40 of the filaments 36 springing back to their initial shape to engage the angle of intersection of the cornea and iris. The flexible, resilient material of the filaments can be any non-toxic, non-degradable material such as a plastic, for example, polypropylene. The filaments preferably have a thickness or diameter in the range of from 0.1 mm to 1.25 mm to enhance flexibility thereof such that a single intraocular lens size can be received in anterior chambers of eyes having varying diameters with the curved free ends of the filaments resiliently flexing to be lodged in the angle between the cornea and the iris.

The lens body 22 preferably has a diameter on the order of magnitude of 6 mm while the distance from the center of the lens body to the free end 40 of each positioning member is in the range of from 7 mm to 7.5 mm, preferably 7.25 mm. The radius of curvature of the fixation filaments adjacent the periphery of the lens body is in the range of from 11 mm to 13 mm, preferably 12 mm; and, the radius of curvature of the fixation filaments at the free ends is in the range of from 7 mm to 7.5 mm, preferably 7.25 mm, the radius of curvature being relatively constant for about 6 mm at the free ends of the filaments.

The fixation and strut filaments can be secured to the lens body in any conventional manner, for example by insertion in a bore in the lens body or by integral formation with the lens body by molding or lathe cutting, it being of primary importance that the filaments remain extremely flexible to minimize trauma and irritation in the eye. The strut and fixation filaments can be secured at intersection point 44 by heat welding if the positioning members are not integrally formed.

As illustrated in FIG. 2, the positioning members 28 and 30 extend in a single plane from the lens body 22; however, if a vaulted configuration is desired to space the lens body from the iris and pupil, the proximal portions 32 of the positioning members 28 and 30 can extend from the lens body at an angle to the planar posterior surface 26 such that the distal portions 34 are spaced from the lens body as shown in FIGS. 3 and 12.

To implant the intraocular lens 20 in an eye, positioning member 30 is inserted in an incision 46 in the eye and the intraocular lens is moved radially into the eye along the direction of the arrow as shown in FIG. 4. Once the intraocular lens is inserted such that approximately half of the lens body is through the incision, the positioning member 28 is grasped by the surgeon with an instrument and rotated in a direction opposite to the curvature of the fixation filament, counterclockwise looking at FIG. 5, while pushing the intraocular lens completely through the incision, the smooth continously curving configuration of the fixation filament facilitating simple non-traumatic placement in the anterior chamber such that the intraocular lens 20 will be received in the anterior chamber in the position shown in FIG. 6. With the intraocular lens fully inserted, the free ends 40 of the fixation filaments will engage the angle of intersection 48 of the cornea 50 and the iris 52 with the lens body 22 positioned in front of the pupil 54, as shown in FIG. 12, it being appreciated that the lens body 22 will lie along the iris when the intraocular lens does not have a vaulted configuration.

The flexible, resilient characteristic of the fixation filaments permits compression of the filaments during implant of the intraocular lens and permits a single intraocular lens size to be implanted in most normal eyes regardless of variations in the diameter of the angle of intersection 48 of the cornea and iris since the resilience or spring-like memory of the filaments assures lodging in the angle of intersection. Accordingly, measurement of the diameter of the angle of intersection is obviated, and the trauma associated with the insertion and removal of an intraocular lens of incorrect size is avoided as well as the problems associated with prior art anterior chamber intraocular lenses when the intraocular lens is either too large or too small. The widened proximal portions of the positioning members prevent pupillary capture of the intraocular lens with the tapered or wedge-like configuration being particularly effective in this regard. The use of the strut filaments also provides two point fixation for the distal portion filament to increase positional stability in the anterior chamber and reduces twisting or turning of the intraocular lens about an axis through the positioning members.

Various modifications of the intraocular lens 20 above described are illustrated in FIGS. 7, 8, 9, 10 and 11, and identical reference numbers are used therein to identify identical parts.

FIG. 7 illustrates an intraocular lens 56 wherein the proximal portions 32 of the positioning members 28 and 30 each includes a central strut filament 58 secured to the lens body 22 and the fixation filament 36 at the intersection point 44 to provide additional fixation for the distal portion filament.

An intraocular lens 60 is shown in FIG. 8 wherein the proximal portions 32 of the positioning members 28 and 30 are formed of a solid web of flexible, resilient material 62 extending from the lens body 22 and preferably integrally formed therewith to increase fixation stability of the distal portion filament.

In the embodiment of FIG. 9, an intraocular lens 64 has the same structure as intraocular lens 20 with the addition of a fixation filament 66 having the same shape and characteristics as fixation filaments 36, the fixation filament 66 extending from the lens body 22 from a position between the positioning members 28 and 30. The fixation filament 66 serves to provide increased stability of the intraocular lens in the anterior chamber.

FIGS. 10 and 11 illustrate intraocular lenses 68 and 70, respectively, having a plurality of fixation filaments 66 extending from the lens body 22 at equally spaced intervals around the periphery of the lens body, intraocular lens 68 having three fixation filaments and intraocular lens 70 having four fixation filaments. By using at least three fixation filaments, the stability of fixation in the anterior chamber is greatly increased since twisting or turning about any axis across the lens body is effectively prohibited and pupillary capture is prevented. Of course, one or more of the fixation filaments 66 could be provided with widened proximal portions in the manner of intraocular lenses 20, 56 or 60.

Surgical implantation of the intraocular lenses 56, 60, 64, 68 and 70 is accomplished in the same manner as described above relative to intraocular lens 20 by simply turning or dialing the intraocular lenses through the incision, and the intraocular lenses 56, 60, 64, 68 and 70 are made of the same materials with the same dimensions in either uniplanar or vaulted configurations.

Inasmuch as the present invention is subject to many variations, modifications and changes in detail, it is intended that all subject matter discussed above or shown in the accompanying drawings be interpreted as illustrative and not in a limiting sense.

What is claimed is:

1. An intraocular lens for implant in the anterior chamber of an eye comprising a lens body having a peripheral edge; and
three positioning members positioned at equal intervals around said peripheral edge of said lens body, each of said positioning members including a flexible, resilient, fixation filament extending from said peripheral edge of said lens body oriented in the same direction relative to said lens body and having a continuous curving configuration throughout the length thereof with a proximal segment adjacent said lens body having a maximum radius of curvature and a distal segment terminating at a free, unattached end having a minimum radius of curvature for positioning in the angle between the cornea and the iris of the eye, said proximal segment extending from said peripheral edge of said lens body at an angle to the tangent thereat less than 90 degrees such that said fixation filament in combination with said lens body produces a smooth curved surface.

2. An intraocular lens as recited in claim 1 wherein said maximum radius of curvature of said proximal segments of said fixation filaments is in the range from 11 mm to 13 mm and said minimum radius of curvature of said distal segments of said fixation filaments is in the range of from 7 mm to 7.5 mm.

3. An intraocular lens for implant in an eye comprising: a lens body having a peripheral edge; and
a plurality of positioning members disposed on said lens body, each of said positioning members including a flexible, resilient, fixation filament extending from said peripheral edge of said lens body and having a continuous curving configuration throughout the length thereof with a proximal segment adjacent said lens body having a maximum radius of curvature and a distal segment terminating at a free, unattached end having a minimum radius of curvature, said proximal segment extending from said peripheral edge of said lens body at an angle to the tangent thereat less than 90 degrees such that said fixation filament in combination with said lens body produces a smooth curved surface and each of said positioning members further including a resilient proximal filament having a first end joined with said fixation filament at a position spaced from said peripheral edge of said lens body and spaced from the center of said lens body by a distance in the range of from 5 mm to 5.5 mm and a second end secured at said peripheral edge of said lens body.

* * * * *